United States Patent [19]

Rezaie et al.

[11] Patent Number: 5,298,599

[45] Date of Patent: Mar. 29, 1994

[54] EXPRESSION AND PURIFICATION OF RECOMBINANT SOLUBLE TISSUE FACTOR

[75] Inventors: Alireza Rezaie, Moore; Charles T. Esmon; James H. Morrissey, both of Oklahoma City, all of Okla.

[73] Assignee: Oklahoma Medical Research Foundation, Oklahoma City, Okla.

[21] Appl. No.: 816,679

[22] Filed: Jan. 3, 1992

Related U.S. Application Data

[63] Continuation-in-part of Ser. No. 730,040, Jul. 12, 1991, Pat. No. 5,202,253, which is a continuation of Ser. No. 292,447, Dec. 30, 1988, abandoned, which is a continuation-in-part of Ser. No. 683,682, Apr. 10, 1991.

[51] Int. Cl.$^5$ ............................................. C07K 13/00
[52] U.S. Cl. ................................. 530/350; 435/68.1; 435/69.7; 435/69.6; 530/381; 530/413; 530/388.25; 530/413
[58] Field of Search ............... 435/68.1, 69.7; 530/350, 413; 536/27

[56] References Cited

U.S. PATENT DOCUMENTS

| | | | |
|---|---|---|---|
| 4,506,009 | 3/1985 | Linhoff et al. | 435/7 |
| 4,851,341 | 7/1989 | Hopp et al. | 435/68 |
| 5,147,638 | 9/1992 | Esmon et al. | 424/85.8 |

FOREIGN PATENT DOCUMENTS

| | | |
|---|---|---|
| 0278776 | 2/1988 | European Pat. Off. . |
| 296413 | 12/1988 | European Pat. Off. . |
| WO88/04692 | 12/1987 | PCT Int'l Appl. . |
| WO88/07543 | 10/1988 | PCT Int'l Appl. . |
| WO88/09817 | 12/1988 | PCT Int'l Appl. . |
| WO90/07524 | 12/1989 | PCT Int'l Appl. . |

OTHER PUBLICATIONS

Long, G. L. (1987) J. Cell. Biochem. 33: 185–90.
Vigano-D'Angelo, et al., (1986) J. Clin. Invest. 77: 416–25.
Morrissey, J. H., et al. (1987) Cell 50: 129–35.
Ghrayeb, J., et al. "Secretion Cloning Vectors in *Escherichia coli*," EMBO Journal, 3(10), 2437–2442 (1984).
Lei, Shau-Ping, et al., "Characterization of the *Erwinia carotovora pelB* Gene and its Product Pectate lyase," J. Bacteriol., 169(9), 4379–4383 (1987).
Pickett, S. K., et al., "A Calcium-Dependent Antibody for Identification and Purification of Recombinant Proteins," Bio Techniques, 7(6) (1989).
deSousa, et al., *Thrombosis Research*, vol. 51, No. 2, pp. 165–173 (1988).
Poggio, et al., *Thrombosis and Haemostasis*, vol. 65, No. 2, pp. 160–164 (1991).
Spicer, et al., *Proceedings of the National Academy of Sciences U.S.A.*, vol. 84, pp. 5148–5152 (Aug. 1987).
Scarpati, et al., *Biochemistry*, vol. 26, No. 17, pp. 5234–5238 (1987).
Fisher, et al., *Thrombosis Research*, vol. 48, No. 1, pp. 89–99 (1987).

(List continued on next page.)

*Primary Examiner*—Robert J. Hill, Jr.
*Assistant Examiner*—David L. Fitzgerald
*Attorney, Agent, or Firm*—Kilpatrick & Cody

[57] ABSTRACT

A method is disclosed to make any protein in a form that can be isolated rapidly from a solution using a specific monoclonal antibody designated "HPC-4". It has now been determined that it is possible to form a fusion protein of the epitope with a protein to be isolated, and isolate the protein using HPC-4-based affinity chromatography. In the preferred embodiment, a specific protease cleavage site is inserted between the epitope and the protein so that the epitope can be easily removed from the isolated protein. In an example, a functionally active soluble tissue factor including the twelve amino acid epitope recognized in combination with calcium by HPC-4 and a factor Xa cleavage site was expressed from a vector inserted into a procaryotic expression system. The recombinant tissue factor can be rapidly isolated in a single chromatographic step using the HPC-4 monoclonal antibody immobilized on a suitable substrate. Once isolated, the Protein C epitope is removed by cleavage with factor Xa, leaving the functionally active, soluble tissue factor.

6 Claims, 3 Drawing Sheets

OTHER PUBLICATIONS

Paborsky, et al., *Biochemistry*, vol. 28, No. 20, pp. 8072-8077 (1989).
Paborsky and Harris, Thrombosis Research, vol. 60, No. 5, pp. 367-376 (1990).
Ruff, et al., *Thrombosis and Haemostasis*, vol. 62, p. 347 (1989).
Ruff, et al., *Journal Biological Chemistry*, vol. 266, No. 4, pp. 2158-2166 (Feb. 5, 1991).
Hoffman, et al., *Journal of Laboratory Clinical MEdicine*, vol. 111, No. 4, pp. 475-481 (Apr. 1988).
Gordon, et al., *Journal of Laboratory Clinical Medicine*, vol. 109, No. 3, pp. 409-413 (Apr. 1987).
K. A. Mitropoulos, *Seminars in Thrombosis and Hemostasis*, vol. 14, No. 3, pp. 246-252 (1988).
Scarabin, et al., *Thrombosis Research*, vol. 45, No. 6, pp. 845-850 (1987).
Esmon et al., Develop. Biol. Standard., 67: 75-82, 1987.
Dreyfus et al., New England Journal of Medecine 325: 1565-1568, 1991.
Seligsohn, et al., The New England Journal of Medicine, vol. 310 No. 9, pp. 559-562 (Mar. 1, 1984).
Vukovich, et al., *British Journal of Haematology* 70, pp. 435-440 (1988).
C. T. Esmon, et al., Joint IABS/CSL Symposium on Standarization in Blood Fractionation including Coagulation Factors, Melbourne, Australia, 1986 *Develop. biol. Standard*, vol. 67, pp. 51-57 (S. Karger, Basel, 1987).
C. T. Esmon, et al., *Journ. of Biol. Chem.* vol. 264. No. 9 pp. 4743-4746 (Mar. 25, 1989).
C. T. Esmon, *Science* vol. 235, pp. 1348-1352 (Mar. 13, 1987).
A. K. Ohlin, et al., *Journ. of Biol. Chem.* vol. 262, No. 28 pp. 13798-13804 (Oct. 5, 1987).
Laurell, et al., *FEBS Letters* vol. 191, No. 1, pp. 75-81 (Oct. 1985).
Abstract 846, Ohlin, et al., *Thrombosis and Haemostasis* 58 (1): 230 (Jul. 1987).
Abstract 848, Freyssinet, et al., *Thrombosis and Haemostasis* 58(1): 230 (Jul. 1987).
Suzuki, et al., *J. Biochem.* 97, 127-138 (1985).
Stearns, et al., *Journ of Biol. Chem.*, vol. 263, No. 2, pp. 826-832 (Jan. 15, 1988).
Beckmann, et al., *Nucl. Acids Res.* vol. 13, No. 14 pp. 5233-5247 ((1985).
Taylor et al. J. Clin Invest. 79: 918-25 1987.
Ikeda et al. Thromb. Res. 39: 297-306 1985.
Goding et al., "Monoclonal Antibodies" Academic Press 1983 pp. 111-113.
Sugo et al. Thromb. Hernost. 58(10 229 1987.

SEQUENCE LISTING ( 1 ) GENERAL INFORMATION:

( i i i ) NUMBER OF SEQUENCES: 9

( 2 ) INFORMATION FOR SEQ ID NO:1:

(i) SEQUENCE CHARACTERISTICS:
  (A) LENGTH: 12 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
  (A) ORGANISM: Mouse (ix) FEATURE:
  (A) NAME/KEY: Binding-site
  (B) LOCATION: 1..12
  (D) OTHER INFORMATION: /note="Epitope recognized by HPC4 antiprotein C antibody"

(xi) SEQUENCE DESCRIPTION: SEQ ID NO:1:

Glu Asp Gln Val Asp Pro Arg Leu Ile Asp Gly Lys
 1           5                  10

(2) INFORMATION FOR SEQ ID NO:2:

(i) SEQUENCE CHARACTERISTICS:
    (A) LENGTH: 672 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Homo sapiens (ix) FEATURE:
    (A) NAME/KEY: miscrecomb
    (B) LOCATION: 1..6

(ix) FEATURE:
    (A) NAME/KEY: miscrecomb
    (B) LOCATION: 67..72

(xi) SEQUENCE DESCRIPTION: SEQ ID NO:2:

| | | | | | |
|---|---|---|---|---|---|
| CCCGGGACCA | CCAATACTGT | GGCAGCATAT | AATTTAACTT | GGAAATCAAC | TAATTTCAAG | 60 |
| ACAATTTTGG | AGTGGGAACC | CAAACCCGTC | AATCAAGTCT | ACACTGTTCA | AATAAGCACT | 120 |
| AAGTCAGGAG | ATTGGAAAAG | CAAATGCTTT | TACACAACAG | ACACAGAGTG | TGACCTCACC | 180 |
| GACGAGATTG | TGAAGGATGT | GAAGCAGACG | TACTTGGCAC | GGGTCTTCTC | CTACCCGGCA | 240 |
| GGGAATGTGG | AGAGCACCGG | TTCTGCTGGG | GAGCCTCTGT | ATGAGAACTC | CCCAGAGTTC | 300 |
| ACACCTTACC | TGGAGACAAA | CCTCGGACAG | CCAACAATTC | AGAGTTTTGA | ACAGGTGGGA | 360 |
| ACAAAAGTGA | ATGTGACCGT | AGAAGATGAA | CGGACTTTAG | TCAGAAGGAA | CAACACTTTC | 420 |
| CTAAGCCTCC | GGGATGTTTT | TGGCAAGGAC | TTAATTTATA | CACTTTATTA | TTGGAAATCT | 480 |
| TCAAGTTCAG | GAAAGAAAAC | AGCCAAAACA | AACACTAATG | AGTTTTTGAT | TGATGTGGAT | 540 |
| AAAGGAGAAA | ACTACTGTTT | CAGTGTTCAA | GCAGTGATTC | CCTCCCGAAC | AGTTAACCGG | 600 |
| AAGAGTACAG | ACAGCCCGGT | AGAGTGTATG | GGCCAGGAGA | AAGGGGAATT | TAGAGAATAA | 660 |
| CTGCAGTCTA | GA | | | | | 672 |

(2) INFORMATION FOR SEQ ID NO:3:

( i ) SEQUENCE CHARACTERISTICS:
   ( A ) LENGTH: 218 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
   ( A ) ORGANISM: Homo sapiens ( x i ) SEQUENCE DESCRIPTION: SEQ ID NO:3:

```
Gly Thr Thr Asn Thr Val Ala Ala Tyr Asn Leu Thr Trp Lys Ser Thr
 1               5                  10                  15

Asn Phe Lys Thr Ile Leu Glu Trp Glu Pro Lys Pro Val Asn Gln Val
             20                  25                  30

Tyr Thr Val Gln Ile Ser Thr Lys Ser Gly Asp Trp Lys Ser Lys Cys
         35                  40                  45

Phe Tyr Thr Thr Asp Thr Glu Cys Asp Leu Thr Asp Glu Ile Val Lys
     50                  55                  60

Asp Val Lys Gln Thr Tyr Leu Ala Arg Val Phe Ser Tyr Pro Ala Gly
 65                  70                  75                  80

Asn Val Glu Ser Thr Gly Ser Ala Gly Glu Pro Leu Tyr Glu Asn Ser
                 85                  90                  95

Pro Glu Phe Thr Pro Tyr Leu Glu Thr Asn Leu Gly Gln Pro Thr Ile
            100                 105                 110

Gln Ser Phe Glu Gln Val Gly Thr Lys Val Asn Val Thr Val Glu Asp
        115                 120                 125

Glu Arg Thr Leu Val Arg Arg Asn Asn Thr Phe Leu Ser Leu Arg Asp
    130                 135                 140

Val Phe Gly Lys Asp Leu Ile Tyr Thr Leu Tyr Tyr Trp Lys Ser Ser
145                 150                 155                 160

Ser Ser Gly Lys Lys Thr Ala Lys Thr Asn Thr Asn Glu Phe Leu Ile
                165                 170                 175

Asp Val Asp Lys Gly Glu Asn Tyr Cys Phe Ser Val Gln Ala Val Ile
            180                 185                 190

Pro Ser Arg Thr Val Asn Arg Lys Ser Thr Asp Ser Pro Val Glu Cys
        195                 200                 205

Met Gly Gln Glu Lys Gly Glu Phe Arg Glu
    210                 215
```

( 2 ) INFORMATION FOR SEQ ID NO:4:

( i ) SEQUENCE CHARACTERISTICS:
      ( A ) LENGTH: 160 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Escherichia coli ( i x ) FEATURE:
      ( A ) NAME/KEY: miscfeature ( B ) LOCATION: 10..13
                    ( D ) OTHER INFORMATION: /note="Shine-Dalgarno sequence"

( i x ) FEATURE:
                    ( A ) NAME/KEY: miscfeature
                    ( B ) LOCATION: 22..85
                    ( D ) OTHER INFORMATION: /note="pelB leader peptide"

( i x ) FEATURE:
                    ( A ) NAME/KEY: miscfeature
                    ( B ) LOCATION: 3..14
                    ( D ) OTHER INFORMATION: /note="HPC-4 epitope"

( i x ) FEATURE:
                    ( A ) NAME/KEY: miscfeature
                    ( B ) LOCATION: 15..18
                    ( D ) OTHER INFORMATION: /note="Factor Xa cleavage site"

( i x ) FEATURE:
                    ( A ) NAME/KEY: miscfeature
                    ( B ) LOCATION: 146..152
                    ( D ) OTHER INFORMATION: /note="NotI restriction enzyme"

( x i ) SEQUENCE DESCRIPTION: SEQ ID NO:4:

```
CTAGATAACG AGGGCAAAAA ATGAAATACC TATTGCCTAC GGCAGCCGCT GGATTGTTAT      60

TACTCGCTGC CCAACCAGCC ATGGCCGAAT TCGAAGATCA GGTAGATCCG CGGTTAATCG     120

ATGGTAAGAT TGAAGGAAGG CCTAGGCGGC CGCAAGCTTG                           160
```

( 2 ) INFORMATION FOR SEQ ID NO:5:

( i ) SEQUENCE CHARACTERISTICS:
                    ( A ) LENGTH: 160 base pairs
                    ( B ) TYPE: nucleic acid
                    ( C ) STRANDEDNESS: single
                    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
                    ( A ) ORGANISM: Escherichia coli ( i x ) FEATURE:
                    ( A ) NAME/KEY: miscfeature
                    ( B ) LOCATION: 83..88
                    ( D ) OTHER INFORMATION: /note="EcoRI restriction enzyme
                              site"

( i x ) FEATURE:
                    ( A ) NAME/KEY: miscfeature
                    ( B ) LOCATION: 134..139
                    ( D ) OTHER INFORMATION: /note="StuI restriction enzyme
                              site"

( i x ) FEATURE:
                    ( A ) NAME/KEY: miscfeature
                    ( B ) LOCATION: 150..155
                    ( D ) OTHER INFORMATION: /note="HindIII restriction enzyme"

( x i ) SEQUENCE DESCRIPTION: SEQ ID NO:5:

```
TATTGCTCCC GTTTTTTACT TTATGGATAA CGGATGCCGT CGGCGACCTA ACAATAATGA      60

GCGACGGGTT GGTCGGTACC GGCTTAAGCT TCTAGTCCAT CTAGGCGCCA ATTAGCTACC    120

ATTCTAACTT CCTTCCGGAT CCGCCGGCGT TCGAACCTAG                          160
```

( 2 ) INFORMATION FOR SEQ ID NO:6:

( i ) SEQUENCE CHARACTERISTICS:
                    ( A ) LENGTH: 4 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( i x ) FEATURE:
                ( A ) NAME/KEY: Cleavage-site
                ( B ) LOCATION: 1..4
                ( D ) OTHER INFORMATION: /note="Factor Xa Cleavage Site"

( x i ) SEQUENCE DESCRIPTION: SEQ ID NO:6:

Ile Glu Gly Arg
        1

( 2 ) INFORMATION FOR SEQ ID NO:7:

( i ) SEQUENCE CHARACTERISTICS:
                ( A ) LENGTH: 5 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( i x ) FEATURE:
                ( A ) NAME/KEY: Cleavage-site
                ( B ) LOCATION: 1..5
                ( D ) OTHER INFORMATION: /note="Enterokinase Cleavage Site"

( x i ) SEQUENCE DESCRIPTION: SEQ ID NO:7:

Asp Asp Asp Asp Lys
        1               5

( 2 ) INFORMATION FOR SEQ ID NO:8:

( i ) SEQUENCE CHARACTERISTICS:
                ( A ) LENGTH: 3 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( i x ) FEATURE:
                ( A ) NAME/KEY: Cleavage-site
                ( B ) LOCATION: 1..3
                ( D ) OTHER INFORMATION: /note="Thrombin Cleavage Site"

( x i ) SEQUENCE DESCRIPTION: SEQ ID NO:8:

Phe Pro Arg
        1

( 2 ) INFORMATION FOR SEQ ID NO:9:

( i ) SEQUENCE CHARACTERISTICS:
                ( A ) LENGTH: 3 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO

```
( i x ) FEATURE:
        ( A ) NAME/KEY: Cleavage-site
        ( B ) LOCATION: 1..3
        ( D ) OTHER INFORMATION: /note="Thrombin Cleavage Site"

( x i ) SEQUENCE DESCRIPTION: SEQ ID NO:9:

Gly  Pro  Arg
    1
```

EXPRESSION AND PURIFICATION OF RECOMBINANT SOLUBLE TISSUE FACTOR

United States government has rights in this invention by virtue of grants from the National Institutes of Health, grant numbers R01 HL44225 and R01 HL29807.

This is a continuation-in-part of. U.S. Ser. No. 07/730,040 filed Jul. 12, 1991, now U.S. Pat. No. 5,202,253, which is a continuation of U.S. Ser. No. 07/292,447, abandoned, entitled "Monoclonal Antibody against Protein C" filed Dec. 30, 1988 by Charles T. Esmon and Naomi L. Esmon, and a continuation-in-part of pending U.S. Ser. No. 07/683,682 entitled "Quantitative Clotting Assay for Activated Factor VII" filed Apr. 10, 1991 by James H. Morrissey.

This invention is generally in the area of methods for purifying proteins, especially blood clotting proteins, using recombinant technology and an unique epitope of a monoclonal antibody directed against Protein C zymogen.

Methods for purifying proteins have been used for many years and can be generally divided into chromatographic methods, for example, ion exchange chromatography, molecular weight sieving, high pressure liquid chromatography, affinity chromatography, and electrophoretic methods, for example, electrophoresis on agarose or acrylamide gels and isoelectric focusing. The usual disadvantages of all of these methods are that they require the starting material be passed through several processes to remove contaminants to the point where the desired material is substantially pure.

In immunoaffinity chromatography, an antibody to the desired protein or other molecule is immobilized on a chromatographic substrate, the protein mixture is applied to the substrate under conditions allowing the antibody to bind the protein, the unbound material is removed by washing, and the bound protein is eluted using, for example, high or low pH, protein denaturants or chaotropes. The end result is a substantially pure protein which often lacks full biological activity.

A variation of this method is described in U.S. Ser. No. 07/730,040 filed Jul. 12, 1991, which is a continuation of U.S. Ser. No. 07/292,447 entitled "Monoclonal Antibody against Protein C" filed Dec. 30, 1988 by Charles T. Esmon and Naomi L. Esmon, disclosing the properties of the monoclonal antibody, HPC-4. The hybridoma cell line which secretes the monoclonal antibody designated as HPC-4, was deposited with the American Type Culture Collection, 12301 Parklawn Drive, Rockville, Md, on Nov. 2, 1988, and assigned ATCC No. HB 9892. This deposit is available to the public upon the grant of a patent.

HPC-4 binds protein C, not activated protein C (APC), and only in the presence of calcium. Thus, when the antibody is immobilized on an affinity support, protein C can be isolated from either plasma-derived sources or from tissue culture expression systems under extremely mild conditions. This is important in maintaining the biological activity of the product and the stability of the solid support resin. Because activated protein C is not bound under any conditions, the resulting product is completely free of APC.

The antibody binds to a defined region of the protein C molecule that is contained within residues 6 and 17 of the heavy chain, specifically E D Q V D P R L I D G K. This peptide can be immobilized directly on a solid support resin and can be used to isolate the antibody in high concentrations from mouse ascites fluid or tissue culture supernatants. This approach allows the isolation of the antibody in extremely pure form in high yield, even from very dilute solutions. The antibody can be removed from the solid support peptide either by the removal of calcium ions, if desired, or by 1.5 M guanidine, which does not affect the function of the purified monoclonal antibody.

It would be advantageous if the purification methods using the Protein C epitope in combination with HPC-4 could be applied to the purification of other proteins, especially blood clotting proteins One such system using a completely different antibody has been described by Prickett, et al., *BioTechniques* 7(6), 580–589 (1989), using a calcium-dependent antibody that recognizes several of the enterokinase sites that are used for $Ca^{2+}$ coordination, including residues 1, 2, 3, 4, and 7 from FIG. 4, p. 583 and Table I, p. 586. This sequence is attached to the N-terminus of the protein to be isolated, and subsequently removed by treatment with urokinase.

It is therefore an object of the present invention to provide a method and means allowing isolation of purified proteins, especially blood clotting proteins, in a single chromatographic step.

It is a further object to provide recombinant proteins having an amino acid sequence specifically bound by a monoclonal antibody.

SUMMARY OF THE INVENTION

A method is disclosed to make any protein in a form that can be isolated rapidly from a solution using a specific monoclonal antibody designated "HPC-4". HPC-4 binds a twelve amino acid epitope of Protein C zymogen recognized in combination with calcium. It has now been determined that it is possible to form a fusion protein of the epitope with a protein to be isolated, and isolate the protein using HPC-4-based affinity chromatography. In the preferred embodiment, a specific protease cleavage site is inserted between the epitope and the protein so that the epitope can be easily removed from the isolated protein. In the most preferred embodiment, the fusion protein is formed by expression of a recombinant gene inserted into an appropriate vector.

In an example, a functionally active soluble tissue factor including the twelve amino acid epitope of Protein C zymogen recognized in combination with calcium by a specific antibody to Protein C zymogen ("HPC-4") and a factor Xa cleavage site was expressed from a vector inserted into a suitable procaryotic or eukaryotic expression system. The recombinant soluble tissue factor can be rapidly isolated in a single chromatographic step using the HPC-4 monoclonal antibody immobilized on a suitable substrate. Once isolated, the Protein C epitope is removed by cleavage with factor Xa, leaving the functionally active, soluble tissue factor.

DETAILED DESCRIPTION OF THE INVENTION

Figure 1:
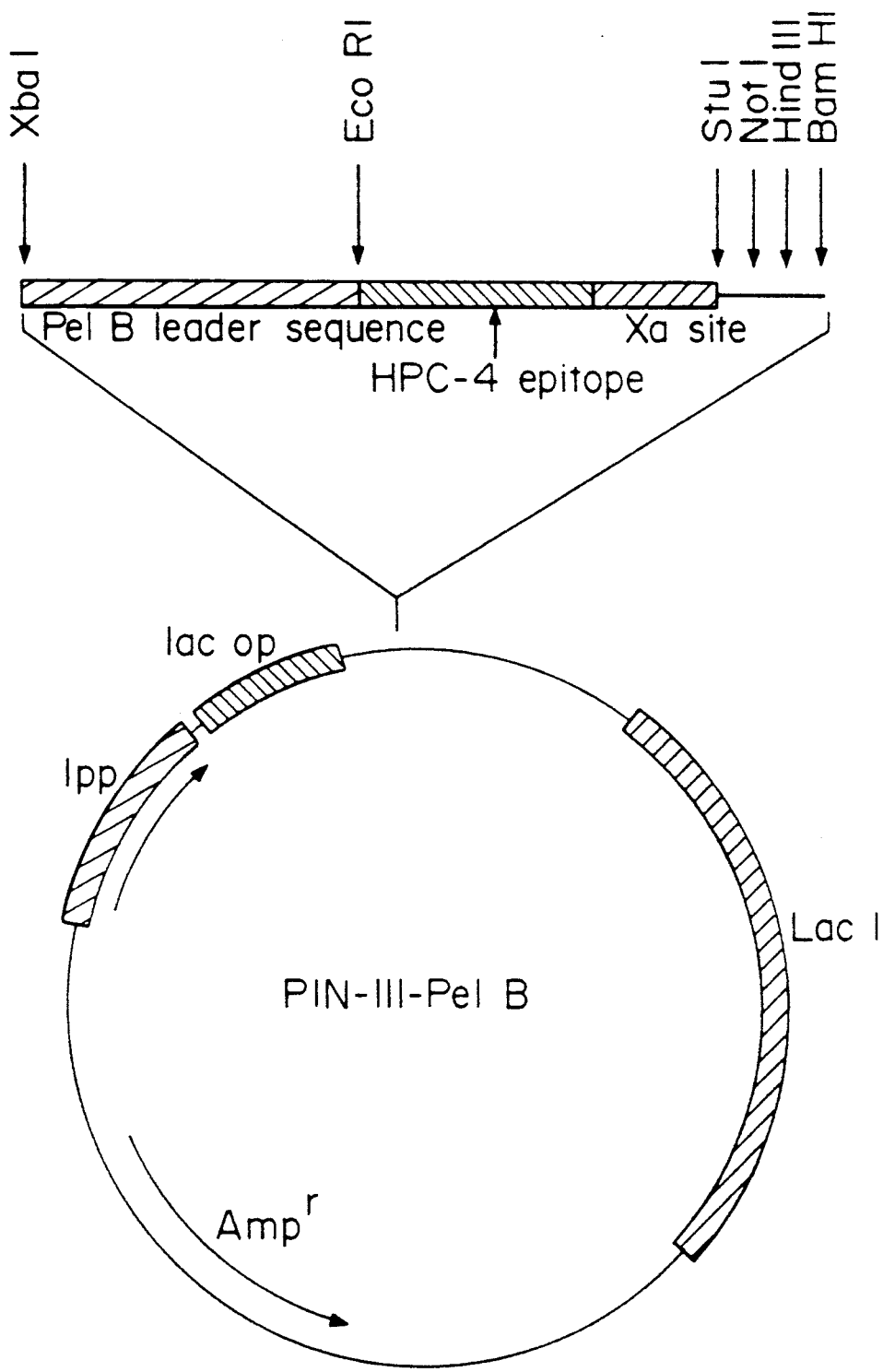
FIG. 1 is expression vector pIN-III-pelB encoding the HPC-4 epitope and factor Xa cleavage site, followed by several restriction enzyme sites for insertion of the gene encoding the protein to be isolated.

A fusion protein readily isolated by affinity chromatography using HPC-4 antibody is prepared by insertion of a DNA sequence encoding the twelve amino acid HPC-4 epitope into a vector, followed by the gene encoding the protein to be isolated. In the preferred embodiment, a specific protease cleavage site is inserted into the vector between the epitope and protein coding sequence, so that the resulting fusion protein can be easily cleaved to yield the epitope peptide and the desired protein.

In the following non-limiting example, a nucleic acid sequence encoding the twelve amino acid residue epitope for HPC-4 is inserted into an expression vector in an orientation such that the expression protein contains the HPC-4 epitope followed by a factor Xa cleavage site and then the amino terminus of tissue factor which has had the signal peptide cytosolictail and transmembrane spanning domains deleted.

The HPC-4 Monoclonal Antibody

The HPC-4 antibody and uses thereof are described in U.S. Ser. No. 07/730,040 filed Jul. 12, 1991, which is a continuation of U.S. Ser. No. 07/292,447 entitled "Monoclonal Antibody against Protein C" filed Dec. 30, 1988 by Charles T. Esmon and Naomi L. Esmon, the teachings of which are incorporated herein. A detailed analysis of the properties of the HPC-4 monoclonal is presented in Stearns, et al., "The Interaction of a $Ca^{2+}$-Dependent Monoclonal Antibody with the Protein C Activation Peptide Region," J. Biol. Chem. 263, 826–832 (1988).

The HPC-4 monoclonal antibody is directed against a peptide sequence present in the activation region of the heavy chain of Protein C and $Ca^{2+}$. This peptide sequence consists of twelve amino acids, glutamic acid-aspartic acid-glutamine-valine-aspartic acid-proline-arginine-leucine-isoleucine-aspartic acid-glycine-lysine (E D Q V D P R L I D G K) (SEQUENCE 1). An advantage of this sequence is that it is short enough to be made synthetically but long enough to impart specificity, thereby avoiding potential cross reactions between the antibody and proteins other than the fusion protein.

The antibody appears to have at least one metal ion binding site in addition to the peptide binding site. The peptide binding activity is responsive to, or "dependent on", binding at the metal ion binding site. The metal ion binding site is capable of binding to a divalent metal cation such as calcium, or a metal having a similar ionic radius and coordination properties such as $Tb^{3+}$. The peptide does not bind $Ca^{2+}$ and hence no $Ca^{2+}$ binding site is added to the fusion protein. This will minimize nonspecific $Ca^{2+}$ mediated interaction with the isolation matrix potentially inherent in the Prickett approach, described at page 3. In the case of tissue factor, it also means that calcium binding to factor VII (the ligand for tissue factor) can be studied without interference due to an additional metal binding site in the tissue factor fusion protein.

When calcium binds to the metal ion binding site in the antibody, the monoclonal antibody becomes significantly more receptive to binding to the peptide. When a metal ion is not bound to the metal ion binding site of the monoclonal antibody, the antigen binding site is relatively unreceptive to binding the antigen. Accordingly, antibody-antigen binding may be controlled by varying the metal ion concentration in the media surrounding the antibody.

Proteins to be Expressed and Purified.

The method described herein is not limited as to the protein that can be expressed as a fusion protein, isolated using HPC-4, then separated from the epitope as the pure protein.

Vectors and Expression Systems

A vector is selected for expression of a sequence encoding the pelB leader peptide HPC-4 epitope and protein to be isolated, preferably separated by a specific protease cleavage site. Examples of suitable bacterial expression vectors which are commercially available include pcDNA II (Invitrogen #V400-20), pNH8a (Stratagene, #215201) and pBTacl (Boehringer Mannheim, #1081365). These vectors are used for expression of full length or partial cDNA sequences in bacteria such as E. coli, where the expressed protein usually accumulates as insoluble aggregates in the cytoplasm of bacteria called inclusion bodies. To extract the target protein, a high concentration (usually 8 M) of a chaotropic agent such as urea is required to dissolve inclusion bodies. This process denatures the protein and results in the inactivation of the target protein. To obtain a functional protein, a refolding step is necessary which is usually very inefficient and difficult to control. Examples of commercially available mammalian expression vectors include pRc/RSV (Invitrogen, #V780-20), pRc/CMV (Invitrogen #V750-20), and pMC1NeO (Stratagene #213201). These expression vectors usually contain a suitable promotor that can direct high-level expression of recombinant proteins in mammalian cells and they also contain a drug resistant gene that can be used for selection of those mammalian cells that have integrated these vectors into their genomes. These vectors are suitable for the expression of full length cDNA and any other DNA fragment which contains a leader peptide at the 5' end of the sequence. These constructs are transferred into a suitable expression system, either procaryotic cells such as E. coli, or eukaryotic cell, such as a yeast or mammalian cell culture system.

It is also possible to insert the cDNA encoding the fusion protein into an embryo for production of a transgenic animal for production of the protein using known methodology. The protein expression can be targeted to a specific tissue using a tissue specific promotor in combination with the protein encoding sequence. For example, the fusion gene is isolated on 1% agarose gel followed by electroelution in a dialysis bag, as described by Maniatis, et al. (1982). The eluted DNA is precipitated, redissolved in water and purified by passing through an elutip-D column as per the instructions of the manufacturer (Schleicher and Schuell, Inc., Keene, NH). The purified DNA is dissolved in 5 mM Tris (pH 7.4) and 0.1 mM EDTA at 3 μg/ml concentration for microinjection.

Mice or other suitable animals such as rabbits or sheep embryos are obtained from commercial suppliers. Reagents such as bovine serum albumin, gelatin, and pronase are obtained from Sigma Chemical Co , St. Louis, MO. Hormones for superovulation, PMS and hCG, are obtained from Organon, Inc., NJ. Hyaluronidase is purchased from Sigma. Restriction enzymes are obtained from New England Biolabs, Beverly, MA. The micromanipulator made by Nara Shige, USA, Inc., Rainin Instruments Co., Woburn, MA can be used to microinject DNA into the pronuclei. DMEM, fetal bovine serum, and DPBS can be obtained from GIBCO Laboratories, Gaithersville, MD.

For construction of transgenic mice, procedures for embryo manipulation and microinjection are described in "Manipulating the Mouse Embryo" by B. Hogan, F. Costantini and E. Lacy (Cold Spring Harbor Laboratory, 1986). Similar methods are used for production of other transgenic animals. Mouse zygotes are collected from six week old females that have been superovulated with pregnant mares serum (PMS) followed 48 hours later with human chorionic gonadotropin. Primed females are placed with males and checked for vaginal plugs on the following morning. Pseudopregnant females are selected for estrus, placed with proven sterile vasectomized males and used as recipients. Zygotes are collected and cumulus cells removed by treatment with hyaluronidase (1 mg/ml). Pronuclear embryos are recovered from female mice mated to males. Females are treated with pregnant mare serum, PMS, (5 IU) to induce follicular growth and human chorionic gonadotropin, hCG (51 U) to induce ovulation. Embryos are recovered in a Dulbecco's modified phosphate buffered saline (DPBS) and maintained in Dulbecco's modified essential medium (DMEM) supplemented with 10% fetal bovine serum.

Microinjections can be performed using Narishige micromanipulators attached to a Nikon diaphot microscope. Embryos are held in 100 microliter drops of DPBS under oil while being microinjected. DNA solution is microinjected into the largest visible male pronucleus. Successful injection is monitored by swelling of the pronucleus. Immediately after injection embryos are transferred to recipient females, mature mice mated to vasectomized male mice. Recipient females are anesthetized using 2,2,2-tribromoethanol. Paralumbar incisions are made to expose the oviducts and the embryos are transformed into the ampullary region of the oviducts. The body wall is sutured and the skin closed with wound clips. Recipients are appropriately ear notched for identification and maintained until parturition.

At three weeks of age about 2-3 cm long tail samples are excised for DNA analysis. The tail samples are digested by incubating overnight at 55° C. in the presence of 0.7 ml 50 mM Tris, pH 8.0, 100 mM EDTA, 0.5% SDS and 350 μg of proteinase K. The digested material is extracted once with equal volume of phenol and once with equal volume of phenol:chloroform (1:1 mixture). The supernatants are mixed with 70 μl 3 M sodium acetate (pH 6.0) and the DNAs are precipitated by adding equal volume of 100% ethanol. The DNAs are spun down in a microfuge, washed once with 70% ethanol, dried and dissolved in 100 μL TE buffer (10 mM Tris, pH 8.0 and 1 mM EDTA). 10 to 20 μl of DNAs were cut with BamHI and Bgl11 or EcoRI, electrophoresed on 1% agarose gels, blotted onto nitrocellulose paper and hybridized with $^{32}$P-labeled DNA sequences. Transgenic animals are identified by autoradiography.

The transgenic females are mated. At five days following parturition milk samples were taken and assayed for the fusion protein. At six to seven weeks of age transgenic males are mated. The F1 litters are analyzed for transgene. The positive females are kept and mated at five weeks of age. At five days following parturition milk samples are assayed for the fusion protein. Milk samples (50-200 μl) are collected from anesthetized mice injected with 0.05 units of oxytocin, an inducer of lactation. The milk is collected in a glass capillary with the aid of mammary palpation. The fusion protein is then isolated by binding to the HPC-4 antibody.

Purification using the HPC-4 antibody-epitope.

The antibody can be bound to a variety of substrates, for use in purification and isolation of the fusion protein, including agarose, acrylamide and other types of conventional chromatographic resins, filters, etc. These materials are known to those skilled in the art, as are the methods for attaching the protein to them. The selection of the material will depend in large part on the scale of the purification or the sample to be analyzed, as well as biocompatibility and government agency approval where the end-product is for pharmaceutical use.

Protease Cleavage Site.

In the most preferred embodiment, the fusion protein includes a protease cleavage site between the epitope and the protein to be isolated. Suitable sites include sequences cleaved by Factor Xa: Ile Glu Gly Arg (IEGR), enterokinase: Asp Asp Asp Asp Lys (DDDDK), and thrombin: Phe/Gly Pro Arg (F/GPR).

Following purification with the HPC-4, the fusion protein is treated with the appropriate enzyme to cleave the binding peptide from the desired protein.

The present invention will be further understood by reference to the following non-limiting examples.

EXAMPLE 1

Construction of a vector for expression of a fusion truncated tissue factor.

Blood coagulation results from the production of thrombin, a proteolytic enzyme inducing platelet aggregation and cleaving fibrinogen to fibrin, which stabilizes the platelet plug. A number of proenzymes and procofactors circulating in the blood interact in this process through several stages during which they are sequentially or simultaneously converted to the activated form, ultimately resulting in the activation of prothrombin to thrombin by activated factor X (fXa) in the presence of factor Va, ionic calcium, and platelets.

Factor X can be activated by either of two pathways, termed the extrinsic and intrinsic pathways. The intrinsic pathway, or surface-mediated activation pathway, consists of a series of reactions where a protein precursor is cleaved to form an active protease, beginning with activation of factor XII to factor XIIa, which converts factor XI to factor XIa, which, in the presence of calcium, converts factor IX to factor IXa. Factor IX can also be activated via the extrinsic pathway by tissue factor (TF) in combination with activated factor VII (factor VIIa; fVIIa). The activated factor IX, in the presence of calcium, phospholipid (platelets), and factor VIIIa, activates factor X to factor Xa.

Physiologically, the major pathway involved in coagulation is believed to be the extrinsic pathway, an essential step of which is activation of factor VII to factor VIIa. Clotting assays and other activity assays designed to measure factor VII and VIIa generally must employ TF, the cofactor required for factor VIIa coagulant activity. Most commonly, TF is provided as a relatively crude preparation known as thromboplastin. Tissue factor is an integral membrane glycoprotein having a protein and a phospholipid component. It has been isolated from a variety of tissues and species and reported to have a molecular mass of between 42,000 and 53,000. DNA encoding tissue factor and methods for expression of the protein have now been reported, for example, in European Patent Application 0 278 776 by Genentech, Inc. and by J. H. Morrissey, et al. Cell 50, 129–135 (1987).

The nucleotide (SEQUENCE 2) and amino acid (SEQUENCE 3) sequence of truncated tissue factor (tTF) is shown below, which, as described below, was modified from the sequence described in U.S. Ser. No. 07/683,682 filed Apr 10, 1991, the teachings of which are incorporated herein. The truncated tissue factor protein lacks the predicted transmembrane and cytoplasmic domains of tissue factor. The essential difference between truncated tissue factor and wild-type tissue factor is that truncated tissue factor is no longer tethered to the phospholipid membrane surface. Soluble tissue factor is a cofactor for activated factor VII (FVII) but not precursor factor VII (FVII). Intact tissue factor is a cofactor for FVII and FVIIa. The SmaI site at the 5! end, and the XbaI site at the 3' end are underlined. The first three nucleotides of the SmaI site are removed upon digestion with the restriction enzyme, SmaI. This permits the tTF cDNA sequence to be blunt-end ligated to StuI site of the pIN-III-pelB-HPC-4 expression vector in a manner that preserves the reading frame of the tTF cDNA clone.

Construction of pIN-III-pelB Expression Vector:

This vector is derived from pIN-III-ompA (John Ghrayeb et al, EMBO J. 3(10):2437–2442 (1984)). Cleavage of pIN-III-ompA with XbaI and BamHI removes a DNA fragment which contains the Shine-Dalgarno sequence GAGG, and the entire nucleotide sequences encoding for the ompA signal peptide. As shown in FIG. 1, by ligation of 8 overlapping oligonucleotides (four sense and the other four complementary antisense), a DNA fragment was synthesized which contains the missing Shine-Dalgarno sequence followed by oligonucleotides sequence encoding a 22 residue long peptide representing the pelB signal peptide (Sahu-Ping Lei, et al, J. Bacteriol. 169(9):4379–4383, 1987) (AA −22 to −1) (SEQUENCE 4).

An EcoRI restriction site was included in this DNA fragment, immediately after the pelB leader sequence, which encodes two extra residues Glu, Phe (+1 and 2). The DNA fragment also encodes a 12 amino acid residue long peptide (residue 3 to 14), which is the epitope for the Ca++ dependent monoclonal antibody HPC-4. The EcoRI restriction site separates the HPC-4 epitope from the pelB signal peptide. Following the nucleotides encoding the epitope, are the nucleotides encoding the four amino acid residues Ile, Glu, Gly, and Arg, forming a factor Xa cleavage site (SEQUENCE 6).

The factor Xa cleavage site is followed by a sequence containing several restriction enzyme sites for cloning of the target gene into this vector for expression. As shown in FIG. 1, this DNA fragment contains an XbaI sticky end at the 5' end and a BamHI sticky end at the 3' end for ligation to the XbaI and BamHI sites of pIN-III-ompA. Multiple cloning sites of pIN-III-pelB includes StuI, Not I, HindIII, and BamHI. StuI is a 6 bp blunt end cutter whose recognition site is AGG CCT; when it cleaves this site it leaves three nucleotides at the 3' end of the DNA fragment, AGG, which encode the last residue in the FXa cleavage site, Arg. Therefore, double digestion of this vector with StuI and either one of the other 3' end cloning sites (NotI or HindIII or BamHI) provides a suitable directional cloning of the target gene for expression.

The oligonucleotide sequence of a synthetic DNA fragment encoding the pelB leader peptide (AA-22 to −1) (SEQUENCE 4); HPC-4 epitope (AA +3 to 14) (SEQUENCE 1); and the FXa cleavage site (AA 15 to 18) (SEQUENCE 6), are shown below. The Shine-Dalgarno sequence GAGG (S-D) is overlined. The restriction enzyme sites useful for cloning have been outlined, which are EcoRI (between the pelB leader sequence and the HPC-4 epitope which creates two extra amino acids +1 and +2), StuI, NotI, and HindIII. The pelB leader peptide cleavage site which is cleaved by bacterial signal peptidase is shown by an arrow. This DNA fragment was made by ligation of eight overlapping oligonucleotides so that it created a sticky XbaI site at the 5' end and a sticky BamHI site at the 3' end for ligation into the XbaI and BamHI site of the pIN-III-ompA vector. The boundary of oligonucleotides for the sense strand and at the bottom for the complementary antisense strand is shown by bold letters.

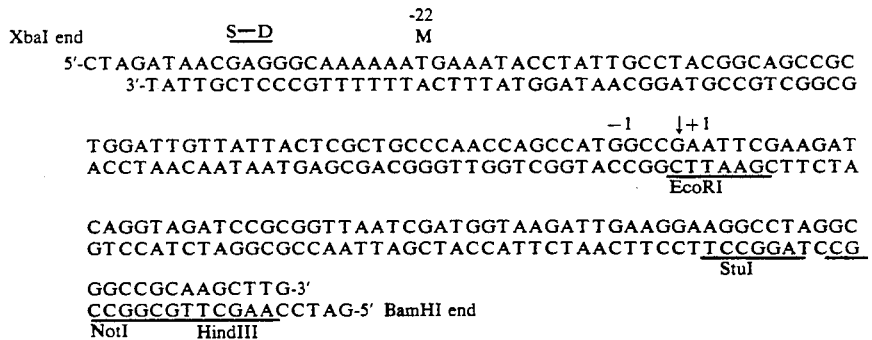

Construction of pIN-III-pelB-tTF

Figure 2:
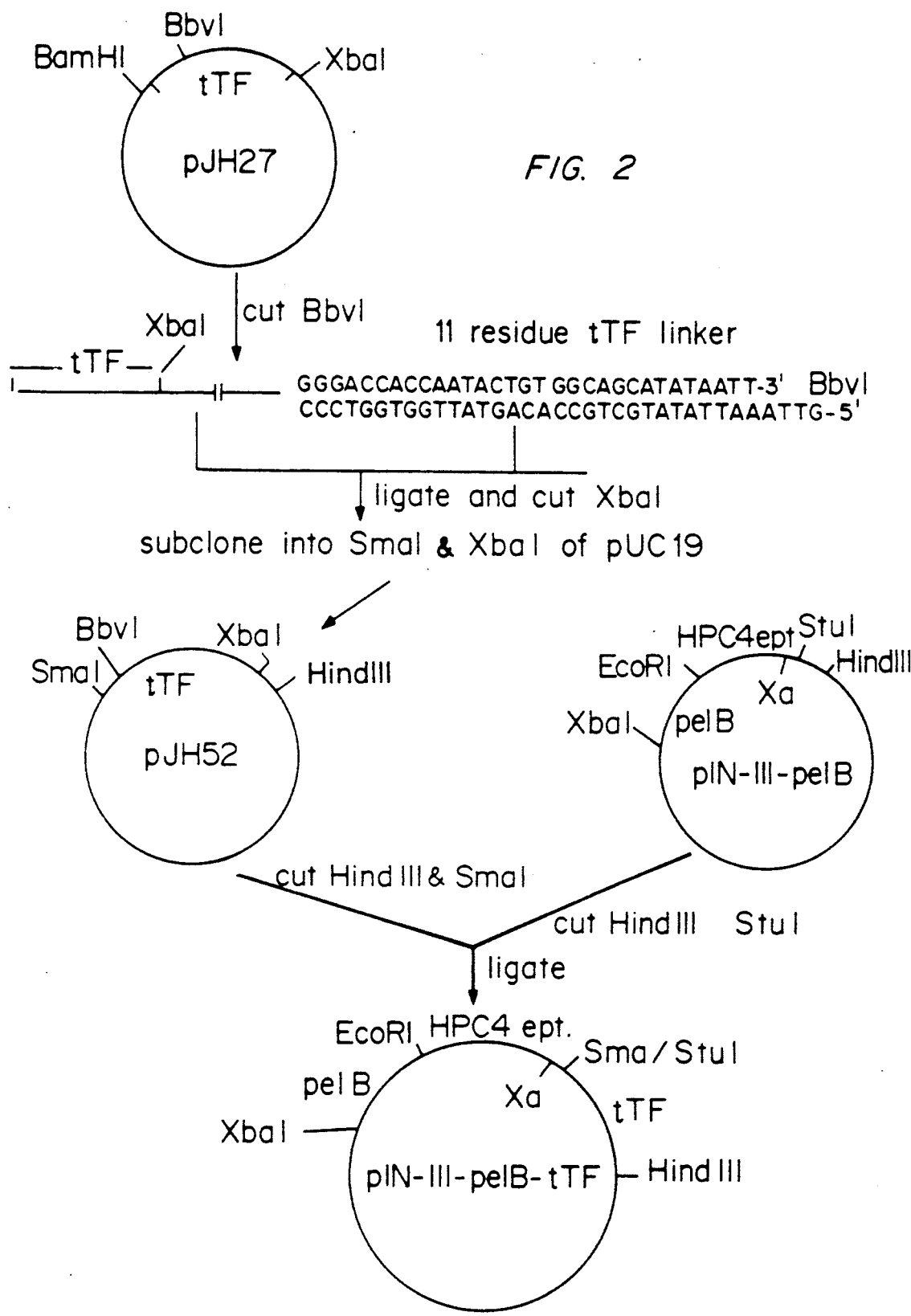
FIG. 2 is a schematic representation of steps involved in the construction of pIN-III-pelB-tTF expression vector. Subcloning of tTF was performed in two stages. At the first stage an intermediary plasmid was prepared which harbored the tTF gene (pUC-tTF). At the second stage the tTF gene was removed from pUC-tTF and subcloned into the pIN-III-pelB (see the text for more detail). The resulting pIN-III-pelB-tTF was used for the transformation of E. coli (XL1-B) for expression.

The construction of pIN-III-pelB-tTF is shown schematically in FIG. 2. pJH27 is a plasmid that contains the entire truncated tissue factor (tTF) cDNA sequence cloned between BamHI and XbaI restriction sites of the vector pGEM-7Zf(+) (Promega). Preparation of the tTF cDNA fragment with 5' and 3' ends compatible with cloning sites in the pIN-III-pelB expression vector was performed in a two-step process. At the first stage the plasmid pJH27 was digested with BbvI restriction enzyme which cleaved away DNA sequences from the 5' end of the cDNA coding for the tF signal peptide and the first 11 residues of the mature tTF protein. In order to repair the tTF gene two complementary oligonucleotides were synthesized, which coded for the 11 missing residues and created a blunt, half-SmaI site at the 5' end. This oligonucleotide contained a sticky end that could hybridize to, and therefore be ligated to, the sticky end of the tTF cDNA sequence created by BbvI digestion.

In the second stage, the modified cDNA insert was removed from pJH27 by digestion with XbaI, and the insert was resolved by agarose gel electrophoresis and purified by elution from the agarose gel. The resulting cDNA fragment which encodes the entire tTF was subcloned into the SmaI and XbaI sites of pUC19 plasmid. As shown in FIG. 2, the tTF cDNA fragment then was removed from pUC19 with SmaI and HindIII restriction enzymes and subcloned into the StuI and HindIII sites of the pIN-III-pelB expression vector.

EXAMPLE 2

Expression and Isolation of the Fusion Protein

Growth of Bacteria for Periplasmic Extract The XL1-B strain of E. coli was grown at 37° C. in LB media. 500 μl of overnight culture was transferred to a 125 ml flask containing 25 ml of LB and 100 μg/ml ampicillin. The flask was shaken at 37° C. for 2-3 hrs until the $OD_{600}$ is equal to 0.6 to 0.7. One liter LB media with ampicillin (Amp) was inoculated with the entire 25 ml bacterial culture and the shaking was continued at 37° C. until the $OD_{600}$=0.6 to 0.7. The culture then was induced with 1 mM isopropyl-B-D-thiogalactopyranoside (IPTG) and the shaking was continued for another 8 hrs at room temperature. The bacterial culture was centrifuged at approximately 3000 rpm for 20 min to separate the culture medium from the cells. The cell pellet was resuspended with 50 ml of cold water and incubated for ½ hour on ice with shaking. The periplasmic extract was then collected by spinning at 10,000 g for ½ hr.

Approximately three-fourths of the protein was expressed in the media of the E. coli, and one-fourth was recovered from the periplasmic space after hypotonic shock. The periplasmic extract was mixed with the culture medium (which has been clarified by centrifugation, as described above), and the mixture was concentrated to approximately one-tenth the original volume using an ultrafiltration spiral cartridge concentrator with a 3000 MW cut-off membrane (Amicon). Following concentration, this material was brought up to 0.1 M NaCl, 0.02 M Tris and 1 mM calcium chloride, and loaded on a HPC-4 column equilibrated with the same buffer (5 mg/ml HPC-4 IgG immobilized on Affi-Gel TM 10; 4 ml total used for 1 liter of starting bacterial culture), washed with approximately 200 ml 1 M NaCl, 0.02 M Tris-HCl, pH 7.5 containing 1 mM $CaCl_2$, followed by approximately 10 to 20 ml of the same buffer but with 0.1 M NaCl, and the protein eluted with 0.1 M NaCl, 0.02 M Tris-HCl, 5 mM EDTA, pH 7.5. Elution of the tTF from the column was monitored by absorbance of light at 280 nm; a single peak of protein was observed.

SDS-PAGE

Figure 3:
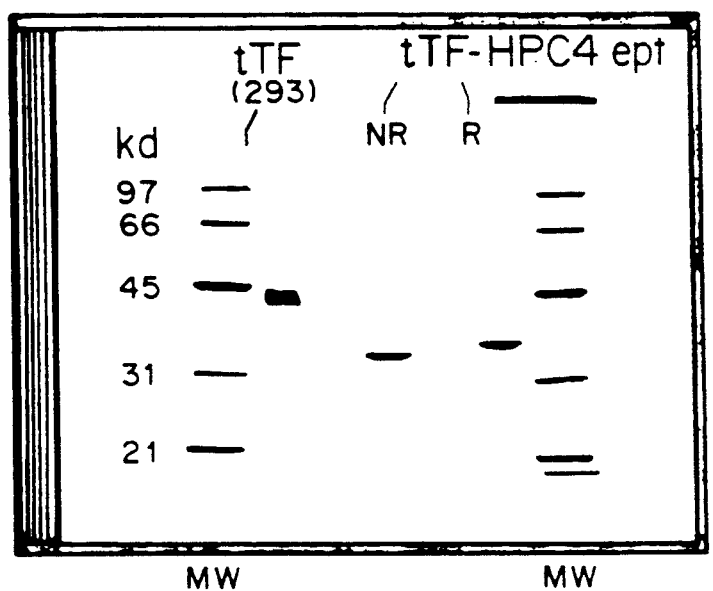
FIG. 3 is a photograph of an SDS gel electrophoresis of the tissue factor, which runs as a monomer in the gel even without disulfide bond reduction.

SDS-PAGE analysis (10% acrylamide using Laemmli system, Laemmli, Nature 227:680-685 (1970)) of the peak fraction from the affinity chromatography indicated a single monomeric band at around 30 kd in both reducing and non-reducing conditions, as shown in FIG. 3. This is consistent with the expected molecular weight of tTF when it is not glycosylated.

Figure 4:
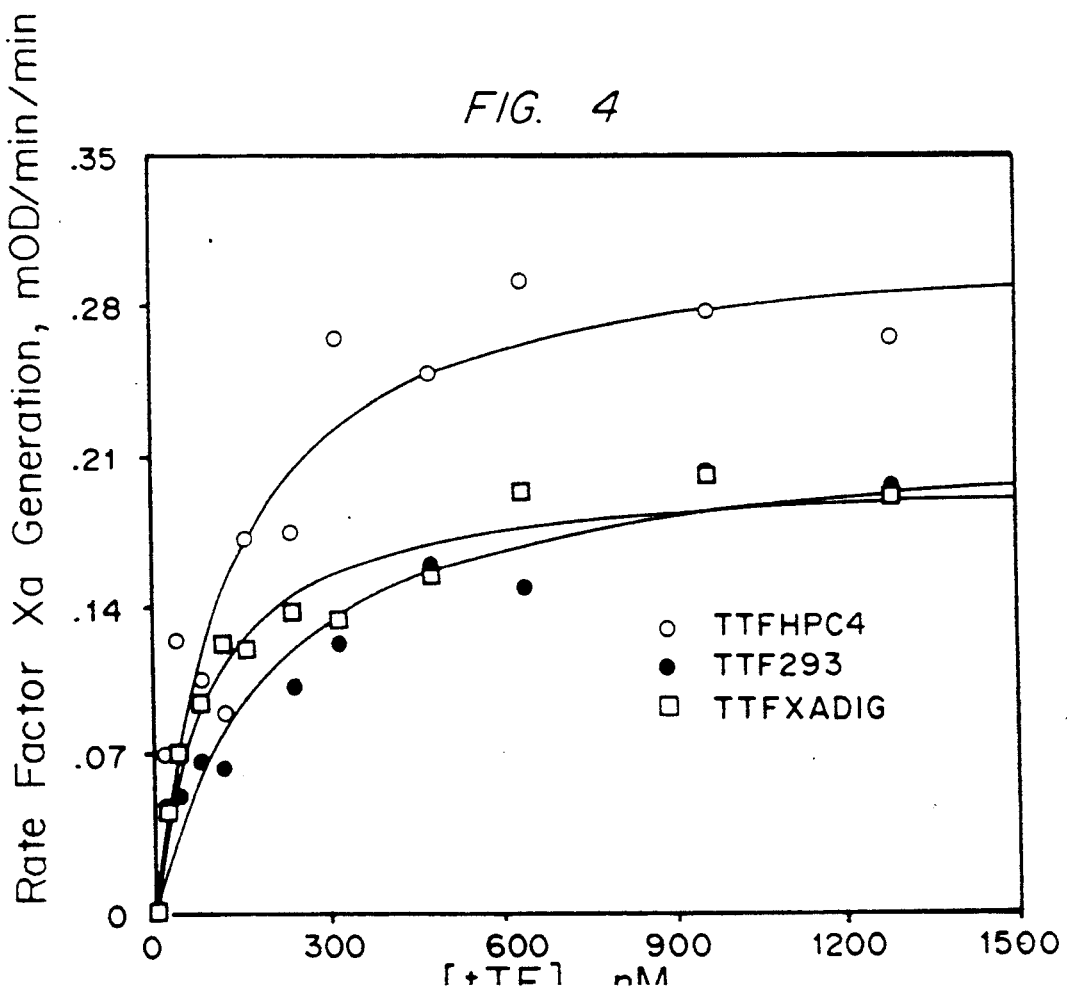
FIG. 4 is a graph of Xa generation rate (m absorbance/min/min) versus tTF (nM) for TTF-HPC-4 (open circles); TTF-293 (closed circles); and TTF-Xa-DIG (open squares).

Approximately 1 mg of soluble tissue factor is recovered from 1 liter of starting bacterial culture, and is homogeneous as shown by SDS gel electrophoresis. The tissue factor runs as monomer in the gel even without disulfide bond reduction. The soluble, truncated tissue factor protein isolated in this manner has full cofactor activity toward factor VIIa even without the HPC-4 epitope removed; this activity is equivalent to that of truncated tissue factor without the HPC-4 epitope expressed in mammalian cells, as shown by FIG. 4.

Functionally the protein is equivalent to the protein expressed in mammalian cell culture, but at less than 10% the cost. This functional equivalence is demonstrated by the factor VIIa concentration dependence on factor X activation and by the ability of the tissue factor from both sources to increase factor VIIa amidolytic activity equivalently.

EXAMPLE 3

Isolation of other proteins using the fusion protein technology in combination with the HPC-4 epitope.

Thrombomodulin fragments, EGF domains of factor X and EGF domains of protein C with the epitope linked to the amino terminal region of these proteins have been expressed in and recovered from other E. coli periplasmic space expression systems. A fragment of thrombomodulin of the 4th-14 6th EGF domains has also been isolated from cultured mammalian cells in a single step purification on the antibody column as described above. In this case, the DNA encoding the thrombomodulin 4th-6th EGF domains was amplified from cDNA by PCR and ligated to synthetic oligonucleotides coding for the transferrin signal peptide followed by the HPC-4 epitope and Xa cleavage site. The resulting DNA fragment was subcloned into a pRc/RSV mammalian cell expression vector for expression in human 293 cells.

Modifications and variations of the method and compositions described herein will be obvious to those skilled in the art from the foregoing detailed description. Such modifications and variations are intended to come within the scope of the following claims.

We claim:

1. A fusion protein comprising an epitope which is capable of binding in the presence of calcium to the monoclonal antibody designated as HPC-4 (ATCC No. HB 9892) and a protein to be isolated by binding of the fusion protein to HPC-4 antibody, wherein the epitope and the protein to be isolated are separated by a specific protease cleavage site.

2. The fusion protein of claim 1 wherein the epitope consists of the amino acid sequence E D Q V D P R L I D G K (SEQ ID NO: 1).

3. The fusion protein of claim 1 wherein the protease cleavage site is selected from the group consisting of amino acid sequences specifically cleaved by Factor Xa; Ile Glu Gly Arg (IEGR, SEQ ID NO; 6), enterokinase: Asp Asp Asp Asp Lys (DDDDK, SEQ ID NO: 7), and thrombin: Phe/Gly Pro Arg (F/GPR, SEQ ID NO: 8 and SEQ ID NO: 9).

4. The fusion protein of claim 1 wherein the protein to be isolated is selected from the group consisting of tissue factor and a protein corresponding to the fourth through sixth epidermal growth factor domains of thrombomodulin.

5. The fusion protein of claim 1 consisting essentially of the amino acid sequence E D Q V D P R L I D G K (SEQ ID NO: 1) at the N-terminus, an amino acid sequence specifically cleaved by factor Xa, and tissue factor.

6. The fusion protein of claim 5 wherein the tissue factor is the extracellular domain of tissue factor.

* * * * *